(12) United States Patent
Schroeder et al.

(10) Patent No.: US 8,346,486 B2
(45) Date of Patent: Jan. 1, 2013

(54) DETERMINING THE QUALITY OF BIOMOLECULE SAMPLES

(75) Inventors: Andreas Schroeder, London (GB); Michael Leiber, Karlsbad (DE); Odilo Mueller, Boston, MA (US); Ruediger Salowsky, Karlsruhe (DE); Susanne Stocker, Munich (DE); Thomas Ragg, Weingarten (DE)

(73) Assignee: Agilent Technologies, Inc., Santa Clara, CA (US)

( * ) Notice: Subject to any disclaimer, the term of this patent is extended or adjusted under 35 U.S.C. 154(b) by 1622 days.

(21) Appl. No.: 10/549,246

(22) PCT Filed: Mar. 29, 2004

(86) PCT No.: PCT/EP2004/050391
§ 371 (c)(1),
(2), (4) Date: Jun. 7, 2006

(87) PCT Pub. No.: WO2004/090780
PCT Pub. Date: Oct. 21, 2004

(65) Prior Publication Data
US 2006/0246577 A1  Nov. 2, 2006

(30) Foreign Application Priority Data
Apr. 5, 2003 (DE) .................. 103 15 581

(51) Int. Cl.
*C12Q 1/68* (2006.01)
*G01N 33/48* (2006.01)
*G01N 33/50* (2006.01)
*G01N 31/00* (2006.01)

(52) U.S. Cl. ................ 702/27; 702/19; 702/20; 702/22; 702/23; 435/6.1

(58) Field of Classification Search ....................... None
See application file for complete search history.

(56) References Cited

U.S. PATENT DOCUMENTS 6,334,099 B1  12/2001  Grace et al.
6,442,491 B1  8/2002  Miller et al.

FOREIGN PATENT DOCUMENTS

| JP | 08-507365 | 8/1996 |
| WO | 98/00708 | 1/1998 |
| WO | 99/45148 | 9/1999 |
| WO | WO 00/66605 | * 11/2000 |
| WO | 0223190 A2 | 3/2002 |

OTHER PUBLICATIONS

Greiner et al. Analysis of biomolecules by Lab-on-a-chip technology. Bioforum, vol. 23, 2000, pp. 751-754. German Article, see Figure 4 on p. 754.*
Allison et al. Transport of charged macromolecules in an electric field by a numerical method: 1. Application to a sphere. Macromolecules, 1992, vol. 25, pp. 3971-3978.*

(Continued)

*Primary Examiner* — Russell S Negin

(57) ABSTRACT

Disclosed is a method for determining the quality, expressed in terms of a quality value, of an biomolecule sample, based on measured data of the biomolecule sample, by extracting a number of prescribed features from the measured data using data analysis, and determining the quality value from the extracted features using a quality algorithm.

22 Claims, 12 Drawing Sheets

OTHER PUBLICATIONS

Allison et al. Modeling the electrophoresis of rigid polyions: Application to lysozyme. Biophysical Journal, vol. 68, 1995, pp. 2261-2270.*

Carbeck et al. Correlations between the charge of proteins and the number of ionizable groups they incorporate: Studies using protein charge ladders, capillary electrophoresis, and Debye-Huckel theory. Journal of the American Chemical Society. vol. 121, 1999, pp. 10671-10679.*

Schmidler et al. Bayesian segmentation of protein secondary structure. Journal of Computational Biology. vol. 7, 2000, pp. 233-248.*

Bruneau P. Search for predictive generic model of aqueous solubility using Bayesian neural nets. J Chem. Inf. Comput. Sci. vol. 41, 2001, pp. 1605-1616.*

Walther G. On a generalization of Blaschke's rolling theorem and the smoothing of surfaces. Mathematical Methods in the Applied Sciences, vol. 22, 1999, pp. 301-316.*

Foley JP. Equations for chromatographic modeling and calculation of peak area. Analytical Chemistry, 1987, vol. 59, pp. 1984-1987.*

Colton et al. Affinity capillary electrophoresis: A physical-organic tool for studying interactions in biomolecular recognition. Electrophoresis, 1998, vol. 19, pp. 367-382.*

Strumberg et al. Conversion of topoisomerase I cleavage complexes on the leading strand of ribosomal DNA into 5'-phosphorylated DNA double-strand breaks by replication runoff. Molecular and Cellular Biology. 2000, vol. 20, pp. 3977-3987.*

Negin et al. Measurement of electrostatic interactions in protein folding with the use of protein charge ladders. Journal of the American Chemical Society, vol. 124, 2002, pp. 2911-2916.*

Pan et al. Folding of RNA involves parallel pathways. Journal of Molecular Biology, vol. 273, 1997, pp. 7-13.*

Definition of "denaturation" Dorland's Illustrated Medical Dictionary, 2007. Retrieved online on Jul. 2, 2010 <<http://www.credoreference.com/entry/ehsdorland/denaturation>>.*

Taylor et al. Use of principal components analysis for mutation detection with two-dimensional electrophoresis protein separations. Electrophoresis, 1992, vol. 13, pp. 162-168.*

Pelle et al. Northern hybridization: rapid and simple electrophoretic conditions. Nucleic Acids Research, 1993, vol. 21, pp. 2783-2784.*

Aggerholm et al. Extensive intra- and interindividual heterogeneity of p15INK4B methylation in acute myeloid leukemia. Cancer Research, 1999, vol. 59, pp. 436-441.*

Craig et al. Ordering of cosmid clones covering the Herpes simplex virus type I (HSV-I) genome: a test case for fingerprinting by hybridisation. Nucleic Acids Research, vol. 18, 1990, pp. 2653-2660.*

Balsamo et al. Transcription of repetitive DNA sequences in Rhynchosciara salivary glands. Cell Differentiation, vol. 2, 1973, pp. 119-130.*

Brewer D: "A Brief Reivew on Microarrays and all that". Feb. 3, 2003.

Dickman B & Watson J: "Procedure for microsatellite-based genotyping". Dec. 5, 2001.

Mueller O, Lightfoot S & Schroeder A: "RNA Integrity Number (RIN)—Standardization of RNA Quality Control". May 1, 2004.

Hill, J.M.: "Ribosomal RNA metabolism during renal hypertrophy. Evidence of decreased degradation of newly synthesized ribosomal RNA." J. Cell Biol. (1975) 64, 260-265; RNA LabChip Kits, Agilent Technologies (2001).

RNA LabChip Kits, Agilent Technologies (2001).

Quantitation comparison of total RNA using the Agilent 2100 bioanalyzer, ribo-green analysis and UV spectrometry, Agilent Technologies (2002).

Advancing the quality control methodology to assess isolated total RNA and generated fragmented cRNA, Agilent Technologies (2003).

Japanese Office Action, Patent Application No. 2006-505504, Mar. 5, 2010, (English Translation).

Japanese Patent Office, Notice of Allowance From Corresponding Japanese Patent Application No. 2006-505504, pp. 1-3; Dec. 14, 2010.

Japanese Patent Office, English Translation of Notice of Allowance From Corresponding Japanese Patent Application No. 2006-505504, pp. 1-3; Dec. 14, 2010.

* cited by examiner

DETERMINING THE QUALITY OF BIOMOLECULE SAMPLES

FIELD OF THE INVENTION

The invention relates to determining the quality of biomolecule samples.

DISCUSSION OF THE BACKGROUND ART

Ribonucleic acids (RNA) are biopolymers contained in cells of all living organisms and in some viruses, which play various roles, primarily conveying the hereditary information of DNA, in constructing proteins. RNA is thus employed in investigations of the genome under microarray-hybridization experiments and RT-PCR, as well as, for example, northern blots, RNase-protection assays, or cDNA-syntheses. The results of such experiments, and the significances of their results, are largely dependent upon the qualities of the RNA samples employed.

The size distributions of RNA biopolymers are measures of the integrity, and thus the qualities, of the RNA samples involved. RNA size distributions vary with the origin of the material involved and the method by which it was prepared, but are significantly affected by contamination by RNA degrading enzymes (RNases) or mechanical shearing forces due to improper handling. In any event, a shift in the lengths of RNA polymers to shorter lengths is observed whenever degradation has occurred.

Traditionally, RNA biopolymers are analyzed by gel electrophoresis. Lab-on-a-chip analyses using the Agilent 2100 Bioanalyzer, as provided by the applicant Agilent Technologies, provide an accurately reproducible, high-resolution, approach to gel-electrophoresis. The Bioanalyzer has become the industry's standard, in particular for RNA analysis. Digital electropherograms obtained using it thus represent ideal starting points for more thorough analyses.

Quality of an RNA molecule can be understood as a measure for its integrity. For example, an RNA sample will exhibit a high degree of integrity, if its molecules have survived extraction from cells or tissues as a whole without suffering degradation or breakage due to shearing forces. A measure for the integrity can indicate e.g. to what extent the sample exhibits signs of degradation or shearing, for example with the highest values displayed by samples that have remained intact during preparation.

Reliable quality determinations have thus far been obtainable using manual, and therefore more or less subjective, methods only. Under manual methods, each individual sample must be visually inspected for integrity by an experienced biochemist before it may be employed in subsequent experiments. Manual quality determinations have become unacceptable as the number of RNA experiments to be performed grew and high-throughput analytical methods appeared.

Methods that will allow estimating the qualities of RNA samples based on a single feature, or only a few features, are known. The best approach that has emerged to date establishes a criterion for the ratio of the areas under the curves for the 28S-rRNA-fragment and the 18S-rRNA-fragment. Theoretically, intact RNA samples will have a ratio of 2. This ratio decreases as degradation progresses, and yields an initial, but relatively inaccurate, means for distinguishing between intact and degraded RNA, since large deviations of this ratio from the theoretical value frequently occur in practice. This criterion is regarded as the state of the art in automatic determination of the qualities of RNA samples.

SUMMARY OF THE INVENTION

While embodiments of the invention can be used for various types of biomolecule samples, it has been shown to be in particular effective and useful for RNA, so that the emphasis in this description shall be on RNA as biomolecular type without limiting the scope of application only on RNA. Examples of other biomolecule samples can be, for example, an RNA sample, a DNA sample, a protein sample, a peptide sample, a sugar sample, a lipid sample, and a modified form of one or more of the aforementioned biomolecule samples Further, embodiments can be applied for various kinds of measured data from an analysis of biomolecule samples. However, electrophoresis has been recognized as an effective and useful separation method for many biomolecules, so that—again—the emphasis in this description shall be on electropherograms representing the measured data from an electrophoretic separation as an example without limiting the scope of application only to electropherograms. Chromatograms would be an example of other kinds of measured data. However, any other type of measured data can be applied accordingly.

Embodiments of the invention allow developing an automatic, reliable determining the qualities of e.g. RNA samples based e.g. on electropherograms. This can be independent of the source and type of the biomolecule material involved, e.g., independent of the biological species, the conditions of the cells, the types of tissues or organs, and the organisms involved, as well as the concentrations of e.g. RNA in the RNA samples and the methods by which they were prepared.

Embodiments allow that biomolecule samples may be characterized by an objective, common, reproducible quality value, which opens up new opportunities for quality control and quality assurance, such as objective comparisons of the qualities of biomolecule samples from various manufacturers and biomolecule samples having various origins, as well as standardized determinations of minimal demands imposed on the quality of the biomolecule sample e.g. RNA employed in various genome experiments.

For example, embodiments may be applied to e.g. RNA samples that have been analyzed using the Agilent 2100 Bioanalyzer and the "Eukaryote Total RNA Nano Assay". The latter assay dictates employment of the RNA 6000 Nano LabChip® Kit, which may be used for analyzing RNA from eukaryotic RNA in nanogram concentrations, i.e., concentrations ranging from 5 ng/µl to 500 ng/µl. "Total RNA" is defined as a preparation of cellular total RNA consisting of mRNA, rRNA, and tRNA.

Embodiments may also be combined with other types of (e.g. RNA) assays available using in particular the Agilent 2100 Bioanalyzer system. For example, "Eukaryote Total RNA Pico Assays" employ picogram-level RNA concentrations. Embodiments may also be employed for determining the qualities of RNA from prokaryotes. The major difference between prokaryotic RNA and eukaryotic RNA is the lengths of their polymers occurring in ribosomal fragments. Further, embodiments may be employed for mRNA-assays ("Eukaryote mRNA Nano", "Eukaryote mRNA Pico", "Prokaryote mRNA Nano", "Prokaryote mRNA Pico"). mRNA-preparations ideally contain exclusively the mRNA-portion of cellular total-RNA.

Similarly, an embodiment would be suited to assess the quality of e.g. protein samples via the "Protein 200 Plus" of the Agilent 2100 bioanalyzer system.

Electrophoresis diagrams are usually referred to as "electropherograms." These diagrams represent plots of the quantities of sample (e.g. RNA) fragments, analyzed as functions of their migration times, which may, for example, be determined using the Agilent 2100 Bioanalyzer or other gel-electrophoresis methods, including for example capillary electrophoresis and chip electrophoresis approaches. The totality of data points on which electropherograms are based are also colloquially termed "electropherograms."

The data points of electropherograms form the input to preferred embodiments. Initially, a few prescribed features ($f_1, \ldots, f_l$) are extracted from the electropherogram involved. Then, the quality value is computed from those features using a quality algorithm.

According to a beneficial embodiment e.g. applied for RNA samples and using electropherograms, the quality algorithm is determined by means of the following processing procedures:

A. collecting a statistically significant number of trial RNA electropherograms covering a prescribed set of RNA samples,
B. assigning a quality label, q, to every electropherogram,
C. extracting as many significant features as possible from the electropherograms using data analysis,
D. determining functional interrelations among the quality labels and certain combinations of features using, for example, an adaptive method,
E. assigning a rating factor, for example, an a posteriori probability determined using the Bayesian method, to every functional interrelation, and
F. specifying the functional interrelation having the greatest rating factor as the quality algorithm.

The number of trial measured data (e.g. electropherograms) collected should be as large as possible. Such trial measured data should accurately reflect the data of genuine applications.

Preferably, all samples are carefully assigned quality labels in advance. These quality labels can represent target values that can later be used for selecting the best combination of features and training the neural network.

The quality of e.g. an RNA sample is a continuously variable parameter, which implies that there are no natural quality classes, which is why discrete quality classes are established under another beneficial embodiment. For example, seven quality classes might be introduced. The worst-quality samples are assigned a quality label of "1" and allocated to the first quality class. Samples that are of slightly better quality are assigned a quality label of "2" and allocated to the second quality class, etc. Finally, the best-quality samples are assigned the quality label "7."

The adaptive approach has the advantages that the best combination of features for determining quality will be automatically selected and quality will be adaptively learned, based on that combination of features.

At this point, the totality of all measured data along with the assigned quality labels, $q \in \{1, \ldots, 7\}$, constitutes the full extent of the knowledge base for further developing the method.

The aim of extracting features from the measured data is extracting as many significant features as possible therefrom. According to embodiments, the electropherograms are subdivided into segments, a preregion, a marker region, a 5S-region, a fast region, an 18S-region, an interregion, a 28S-region, and a postregion, for that purpose.

Each of those segments can then be considered separately and yields several local features peculiar to that particular segment that collectively describe the shape of the particular electropherogram involved within that segment in a sufficiently accurate way. Several global features are also extracted, i.e. features that span several segments. The result of this processing can a list of, for example, around 100 features per electropherogram.

The basis for the data analysis is a list of the maxima, or peaks, appearing in the particular measured data (e.g. electropherogram) involved. Peaks may be detected by integrating the data curve. This integration yields the positions of peaks and their starting points and ending points, along with their heights, widths, and the areas under them.

Following the practice of the Agilent 2100 Bioanalyzer's system software, some peaks can be tagged "ladder peaks," "markers," "18S-peaks," or "28S-peaks." This approach to integration and tagging yields better accuracy and lower vulnerability to anomalies, such as "ghost peaks" or "spikes". According to an embodiment, a linear, statistical model of the positions, heights, and areas of the first four ladder peaks is provided for this purpose. These four peaks of the ladder, which jointly best suit the model, are termed "ladder peaks" and labeled as such.

The first peak of the ladder is the lower marker, whose position, height, and area agree with the positions, heights, and areas of the lower markers of the other samples of a chip, if drifting effects are disregarded. Once again, a statistical model, that, this time, in addition to the positions, heights, and areas of the lower markers, also takes account of the lower markers' drift in the samples of a chip, is set up. Each of the thirteen peaks, one peak for each sample of a chip, that best suit this model is labeled a lower marker.

The interrelation among the positions of the markers and the 18S-peaks and 28S-peaks can then be summarized in a model and the associated peaks labeled as 18S-peaks and 28S-peaks, respectively. In the case of severely degraded RNA samples, 18S-peaks and 28S-peaks will no longer be distinguishable from the background, In that case, the estimated positions of 18S-peaks and 28S-peaks may still be computed based on the preceding tagging in order to allow the subsequent subdivision into segments for all quality classes.

In one embodiment, it has been shown that the labeling that results from employing this approach disagrees with manual labeling of lower markers in only 0.8% of all cases, and from manual labeling of 18S-peaks and 28S-peaks in 1.2% of all cases.

Under an elaboration on embodiments according to the invention and based on the above described tagging approach, every measured data (e.g. electropherogram) can be subdivided into the aforementioned eight contiguous segments covering the entire data area. The segment preceding the lower marker is designated the preregion. The marker region coincides with the area occupied by the lower-marker peak. The respective 18S-regions and 28S-regions cover the 18S-peaks and 28S-peaks, respectively. Two regions, the 5S-region and the fast region, lie between the marker region and the 18S-region. The approximate boundary between these two regions is determined from the positions of the lower marker and the 5.8S/5S/tRNA-peaks of samples containing 5.8S, 5S rRNA, and tRNA and then transferred to all samples, based on the positions of the lower marker. The interregion lies between the 18S-region and the 28S-region. FIG. 1 illustrates the subdivision performed.

Correction e.g. of the electropherogram baseline may substantially follow the practice adopted by the Agilent 2100 Bioanalyzer's system software with some differences. The baseline may ideally remain constant over their preregion and postregion segments if noise is disregarded. Baseline levels may markedly differ from electropherogram to electropherogram. In some cases, their baseline may also slope or even have a wavy shape. The latter case is a clear indication of a problem occurring during data acquisition.

The idea underlying baseline correction is eliminating the constant, or linearly rising or falling, portion of the background from data signals. According to embodiments, an attempt is made to find a straight line that coincides with the data signal, excluding contributions due to noise, i.e., that, on average, differs from the data signal by a noise standard deviation, $\sigma_{noise}$ within the preregion and postregion segments. The equation known from the literature is usually used for computing the noise standard deviation, $\sigma_{noise}$.

The data signal can be normalized to the global-maximum data signal occurring within the 5S-region, the fast region, the 18S-region, the interregion, and the 28S-region before the actual feature extraction commences. The marker region is ignored here in order to allow better handling of differing concentrations. The segments listed above span a slice of the data curve, which is referred to as "utilized section".

In addition to the original data curve, other smoothed data curves can also be employed. A Savitzky-Golay filter and a rolling-ball algorithm, e.g. as described in EP 0 969 283 A1, are preferentially employed for smoothing data curves.

The following local features of any segment may be extracted from original and smoothed data curves:
  the minimum value and the maximum value occurring within the segment,
  the slope and y-intercept of the interpolating straight line fitted into points on the curve falling within the bounds of the segment,
  the y-values of this interpolating straight line at the start and end points of the segment,
  the area under the curve of the segment,
  the area under the interpolating straight line of the segment,
  the ratio of the area under the curve of the segment to the area under the utilized section,
  the ratio of the area under the interpolating straight line of the segment to the area under the utilized section,
  the deviation of the interpolating straight line from the data curve, and
  the deviation of the smoothed data curve from the original data curve.

The following global features can also be extracted:
  the total-RNA-ratio, i.e., the ratio of the total area of the 18S-fragment and 28S-fragment to the total area enclosed within the utilized section,
  the 28/18-ratio, i.e., the ratio of the area of the 28S-fragment to the area of the 18S-fragment,
  the signal/noise ratio,
  the noise standard deviation, and
  the concentration of the sample, which may be computed from the area under the data curve for the ladder having a prescribed concentration and the area under the data curve for the sample.

The totality of features extracted from the measured data (e.g. the RNA electropherograms) and their associated quality labels, q, form the entire knowledge base for the next step, that of determining the functional interrelation among the quality labels and a suitable combination of features. The combination of features to be employed and the functional interrelation involved may be determined using, e.g., an adaptive method.

Choosing a suitable model can be of great importance to the performance of an adaptive method. The more adjustable parameters that the model contains, the more training data will be needed in order to determine a workable functional interrelation. In the case of feed-forward two-layer neural networks, a "model" is defined as the total number of neurons contained in the neural network's input layer and hidden layer. The adjustable parameters involved are the weighting factors of the input neurons with respect to the hidden neurons and the weighting factors of the hidden neurons with respect to the output neurons. Preferably, as few features as possible are chosen as input to the neural network. Such combination of features should convey sufficient information on the quality label.

According to another beneficial embodiment, an iterative forward search that starts off by seeking the feature that yields the most information on the quality label is implemented. Under a second step, the best supplement to the first feature's information content related to the quality label is sought. Further steps of the iterative forward search arrange the features in a list, such that the information content of the last feature added to the list will represent the optimal supplement regarding the quality label of those features already on the list.

At every step of this iterative forward search, the mutual information, i.e., the mutual information content of the combination of features and the quality label, is maximized. The definition of, and information on, mutual information will be found in the relevant literature. The quantumSEL software routine from the quantum software package supplied by the firm quantiom bioinformatics GmbH i.G. may be employed for computing this mutual information. Information on that software and the company are publicly available.

The model itself, i.e., the combination of features to be employed and the number of hidden neurons, can be determined under the steps that follow.

One starts off by attempting to determine the best functional interrelation between the first feature, $f_1$, of the list ($f_1$, ..., $f_n$) and the quality label. The complexity of the single-feature functional interrelation sought may be increased by successively adding hidden neurons. A rating factor may be computed for each such functional interrelation. As the number of hidden neurons increases, the rating factor of the interrelation found will initially increase, and then decrease. The model will initially be insufficiently complex. However, overly complex models incorporate a surplus of parameters whose values can no longer be reliably set using the given database. The feature $f_1$ and number of hidden neurons that yield the maximum of the rating factor represent the best single-feature model for the quality algorithm.

One then attempts to increase the rating factor by successively adding further features from the list and finds the best number of hidden neurons and the resultant rating factor for the combinations of features ($f_1$, $f_2$), ($f_1$, $f_2$, $f_3$), etc., in succession. The rating factor will initially increase, and then decrease. The combination of features, ($f_1$, $f_2$, ..., $f_l$), and associated number of hidden neurons for which the rating factor is maximized represent the model to be employed for the quality algorithm. This procedure is illustrated in FIG. 12.

According to a beneficial embodiment, the rating factors are determined using a Bayesian method. For example, a maximum a posteriori (MAP) approach might be employed. Under the MAP-approach, the a posteriori probability is computed for a given model, based on training data. The a posteriori probability is the rating factor for the model. Adjustment of the weighting factors of the neural network using the model chosen also employs the MAP-approach. Further information on the MAP-approach will be found in the relevant literature.

The MAP-approach can be implemented under the quantumLEAD software routine from the aforementioned quantum software package, and can be employed in the case of the method treated here.

A quality algorithm that computes a quality value from a prescribed combination of features for a given electropherogram can thus be obtained. The computed quality value can be a decimal number, and is preferably interpreted in the context of the quality label introduced. For example, a quality label of 5.8 implies that the electropherogram under study is of slightly worse quality than the average electropherogram in a set of trial electropherograms having a quality label of 6, but is of much better quality than the average electropherogram in a set of trial electropherograms having an average quality label of 5.

According to a beneficial embodiment, both the quality value and the degree to which the sample involved is anomalous are determined. In view of the large number of anomalous cases that are observed e.g. in electropherograms, only those that occur rather frequently or might severely affect the meaningfulness of the quality value are considered. The measured data involved is studied in order to detect the presence of these prescribed anomalous cases, and the quality value is thus enriched by the addition of information on potential anomalies. According to embodiments, the following anomalous cases are prescribed: ghost peaks, spikes, and other anomalies occurring in its preregion, 5S-region, fast region, interregion, and postregion, along with baseline problems.

A few of those features prescribed for each of the anomalous cases involved are preferably extracted from the electropherogram for every anomalous case and the presence of the respective anomalous case computed using an associated anomalous-case algorithm. The result can be a binary vector whose elements indicate whether the electropherogram contains the respective anomalous case involved.

In the event that no anomalous cases are detected, the electropherogram involved may be regarded as free of anomalous cases. Otherwise, it can be regarded as afflicted with anomalous cases. Occurrence of anomalies hinders reliable computation of the quality value. The anomalous cases are thus computed first, and the computation of the quality value aborted in the event that the electropherogram proves to be afflicted with anomalies.

Anomalous cases may be subdivided into critical anomalous cases, such as 5S-region, fast-region, and interregion anomalous cases and baseline problems, and uncritical anomalous cases, such as preregion and postregion anomalous cases. If an uncritical anomalous case should occur, the quality value may still be relatively reliably computed and reported to the user, accompanied by a notification that an uncritical anomalous case is involved. Concerning this matter, reference is made to the degree to which an electropherogram is anomalous, namely, either free of anomalies, afflicted with uncritical anomalies, or afflicted with anomalies.

In order to determine the individual anomalous-case algorithms, the procedures of steps A through F are performed in a manner similar to that used for determining the quality algorithm, except that anomalous-case labels are employed instead of quality labels.

According to embodiments, one obtains a method for determining the qualities of samples once the aforementioned steps have been concluded. The method for determining their qualities is noted for its very high performance and robustness.

Embodiments of the invention can be partly or entirely embodied or supported by one or more suitable software programs, which can be stored on or otherwise provided by any kind of data carrier, and which might be executed in or by any suitable data processing unit.

BRIEF DESCRIPTION OF DRAWINGS

Other objects and many of the attendant advantages of embodiments of the present invention will be readily appreciated and become better understood by reference to the following more detailed description of preferred embodiments in connection with the accompanied drawing(s). Features that are substantially or functionally equal or similar will be referred to with the same reference sign(s).

The figures illustrate several details of the method according to embodiments of the invention. The figures depict.

DETAILED DESCRIPTION OF THE PREFERRED EMBODIMENT

Figure 1:
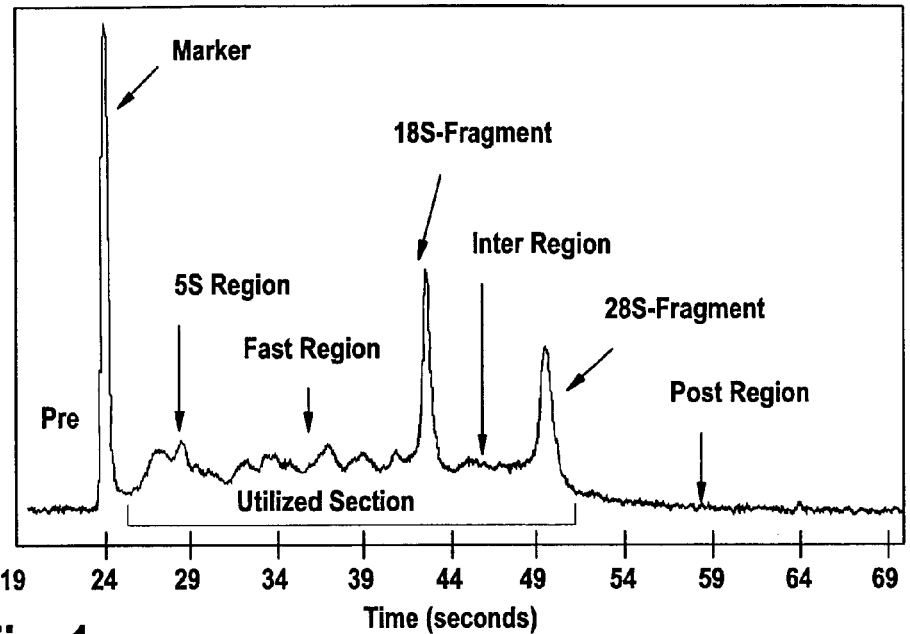
FIG. 1 subdivision of an electropherogram into segments,
FIG. 2 an electropherogram exhibiting a ladder,
FIGS. 3a-3f electropherograms of various RNA samples of various qualities,
FIGS. 4a & 4b electropherograms of RNA samples prepared using various methods,
FIGS. 5a-5f electropherograms of three RNA samples of comparable quality on differing scales,
FIG. 6 an electropherogram where multiple peaks are associated with a single fragment,
FIG. 7 a gel representation of RNA samples,
FIG. 8 an electropherogram exhibiting ghost peaks,
FIGS. 9a & 9b an electropherogram exhibiting a ghost peak,
FIG. 10 an electropherogram exhibiting a spike,
FIGS. 11a-11c electropherograms having various types of baselines
FIG. 12 an illustration of the procedures involved in choosing models,
FIGS. 13a-13b features extracted from the fast region,
FIG. 14 a flowchart illustrating the procedures involved in determining quality values,
FIG. 15 a flowchart illustrating the procedures involved in determining quality algorithms.

FIG. 1 depicts a subdivision of an electropherogram into the eight segments: a preregion, a marker region, a 5S-region, a fast region, an 18S-region, an interregion, a 28S-region, and a postregion. The boundaries of these regions have been omitted.

Figure 2:
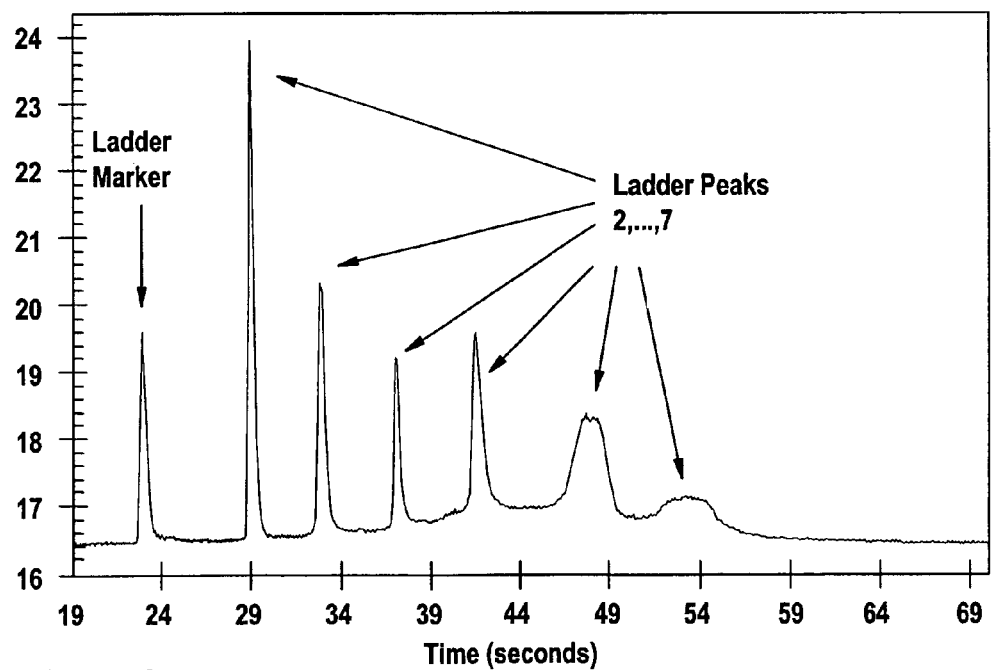
Figure 3:
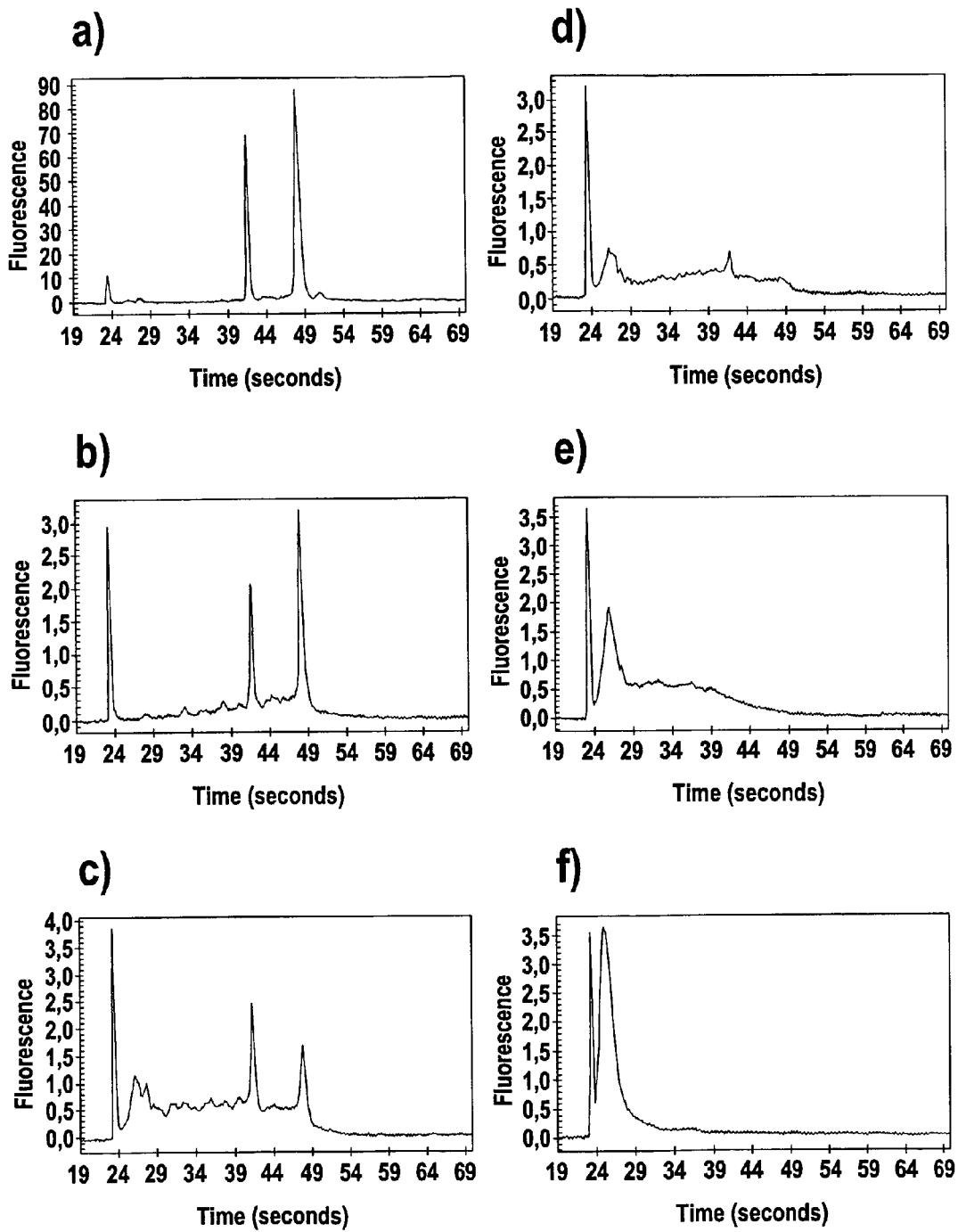

FIG. 2 depicts a typical ladder containing seven RNA-fragments of known lengths and concentrations prescribed by the assay. Its electropherogram is analyzed and employed for quantification.

FIGS. 3a-3f depict electropherograms of total-RNA samples of various qualities in the order of decreasing quality, i.e., their quality decreases from FIG. 3a to FIG. 3f. In addition to their lower marker, their initial peak, RNA samples of good quality also exhibit clearly recognizable peaks in their 18S-rRNA-fragments and 28S-rRNA-fragments. The peaks in their rRNA-fragments become increasingly less pronounced as their quality decreases, until they may no longer be distinguished from the background. A mound of degraded RNA that shifts to the left, toward shorter migration times, and thus toward lower molecular weights, simultaneously forms.

Figure 4:
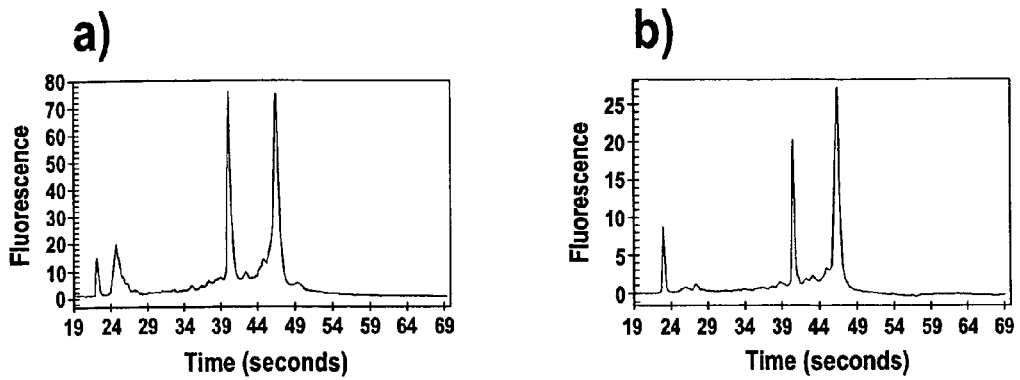

FIG. 4 depicts electropherograms of total-RNA-samples of comparable qualities and concentrations. The differences in their 5S-regions, which may contain both 5.8S and 5S rRNA, as well as tRNA, largely depend upon the method employed for their preparation. The electropherogram shown in FIG. 4a contains a large quantity of RNA in its 5S-region. The 5.8S and 5S rRNA fraction, as well as the tRNA portion in the sample of FIG. 4b were largely filtered out during preparation.

Figure 5:
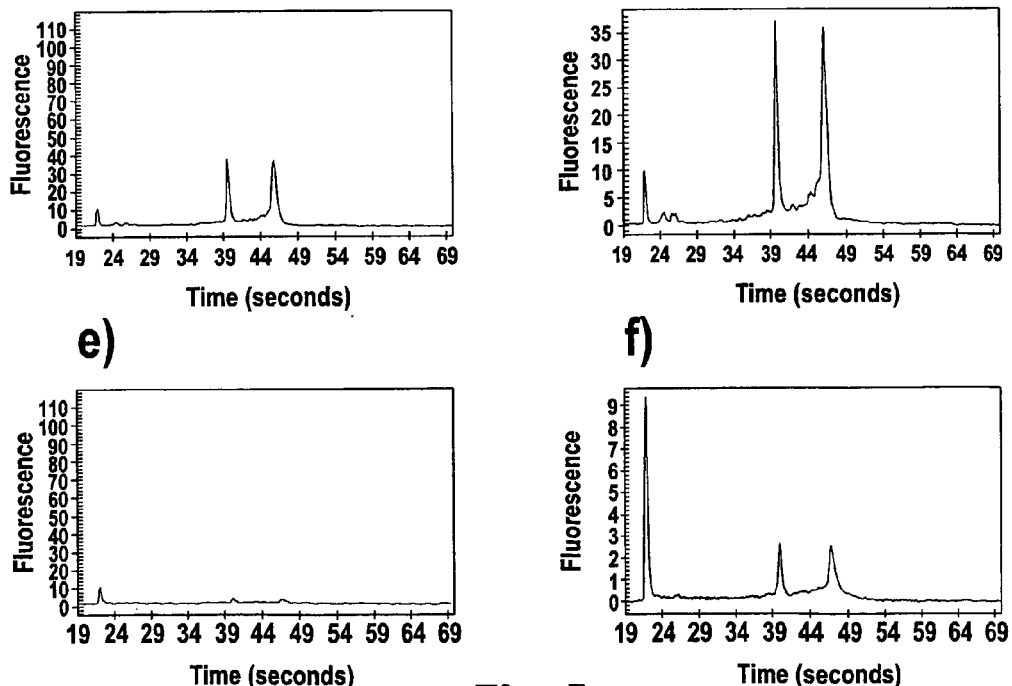

FIG. 5 depicts electropherograms of three RNA samples of comparable qualities having concentrations of 2 mg/µl, 250 ng/μl, and 25 ng/μl, respectively. FIGS. 5a, 5c, and 5e represent electropherograms of RNA samples for the case where a common scaling factor is employed. The concentrations of their markers are prescribed by the total-RNA-nanoassays. If a common scaling factor is employed, their markers will all have the same height, while the heights of the peaks in their 18S-regions and 28S-regions will vary. FIGS. 5b, 5d, and 5f depict electropherograms of the same samples for the case where differing scaling factors are employed.

Figure 6:
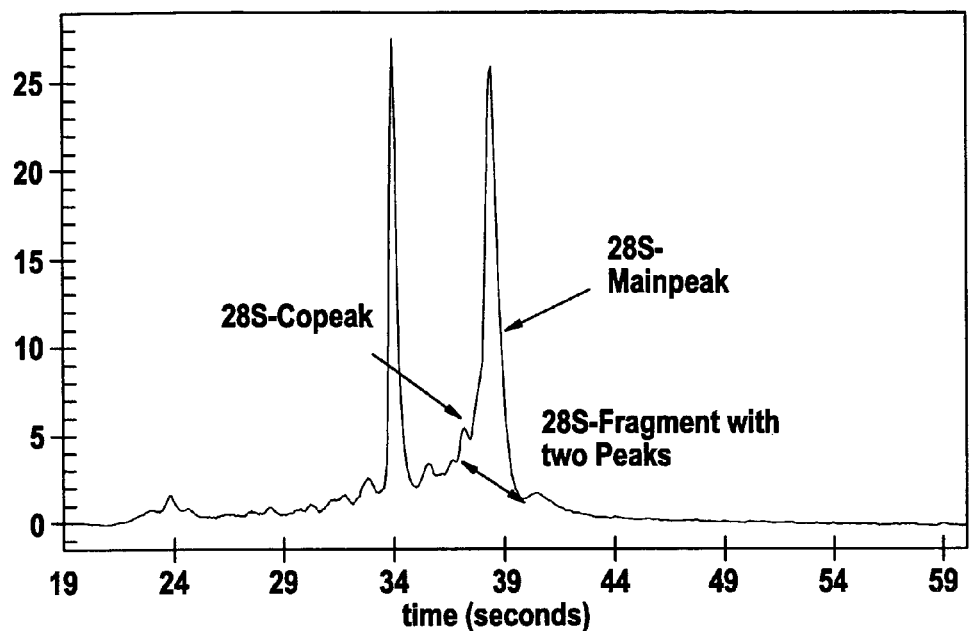

FIG. 6 depicts both the main 28S-peak and a well-defined 28S-copeak.

Figure 7:
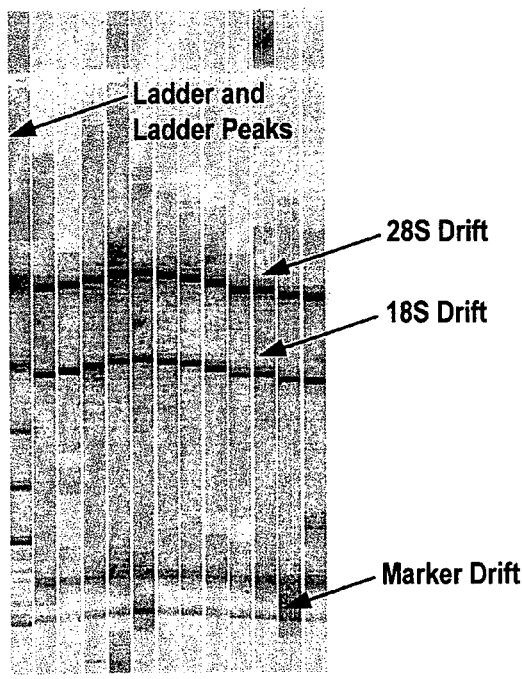

FIG. 7 depicts a gel representation of RNA samples that simulates the appearance of a gel, such as that that arises in the case of gel electrophoresis and may be obtained from the resultant electropherogram. Sharp, thin bands in this gel representation correspond to well-defined, sharp peaks. The broader, gray bands correspond to wavy prominences. This gel representation is particularly suited to displaying drifting effects. The figure depicts the thirteen samples of a chip. The first sample contains the ladder. The ladder contains RNA-fragments predefined by the assay employed, and is co-analyzed for every chip in order to allow the optional normalizations and concentration determinations. The other twelve samples contain the actual RNA samples involved. The figure illustrates the typical drifting effect. Markers and the 18S-peaks and 28S-peaks form wavy curves in the case of all samples.

Figure 8:
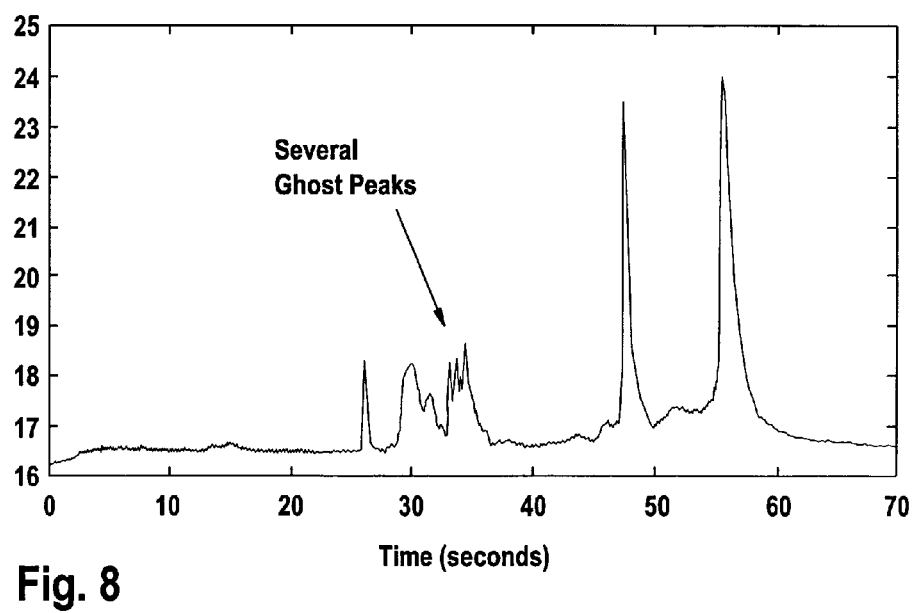

FIG. 8 depicts an electropherogram exhibiting several, disturbing, ghost peaks.

Figure 9:
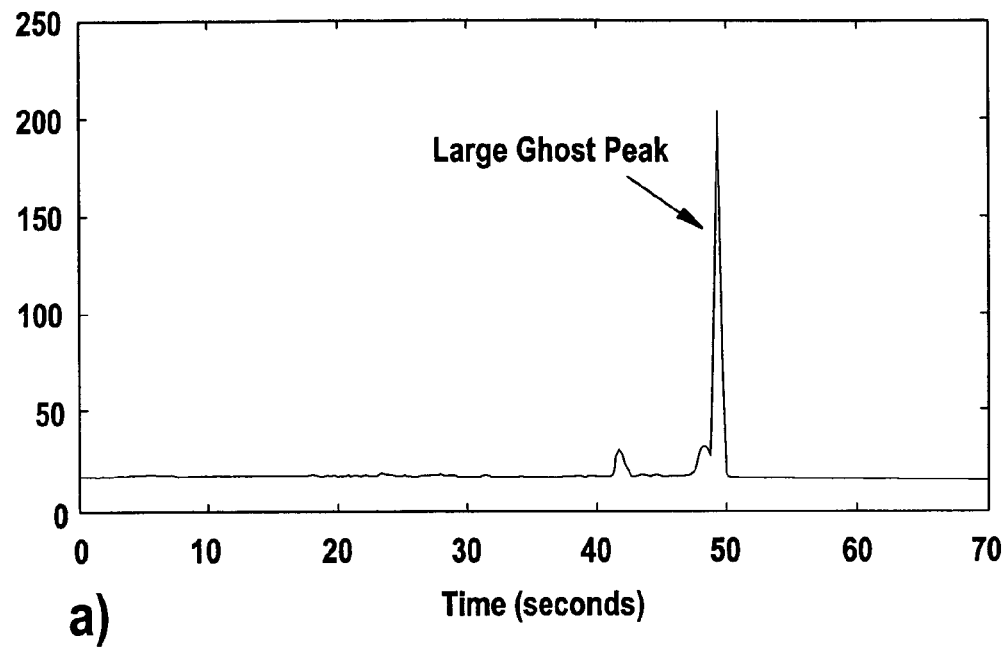
Figure 9:
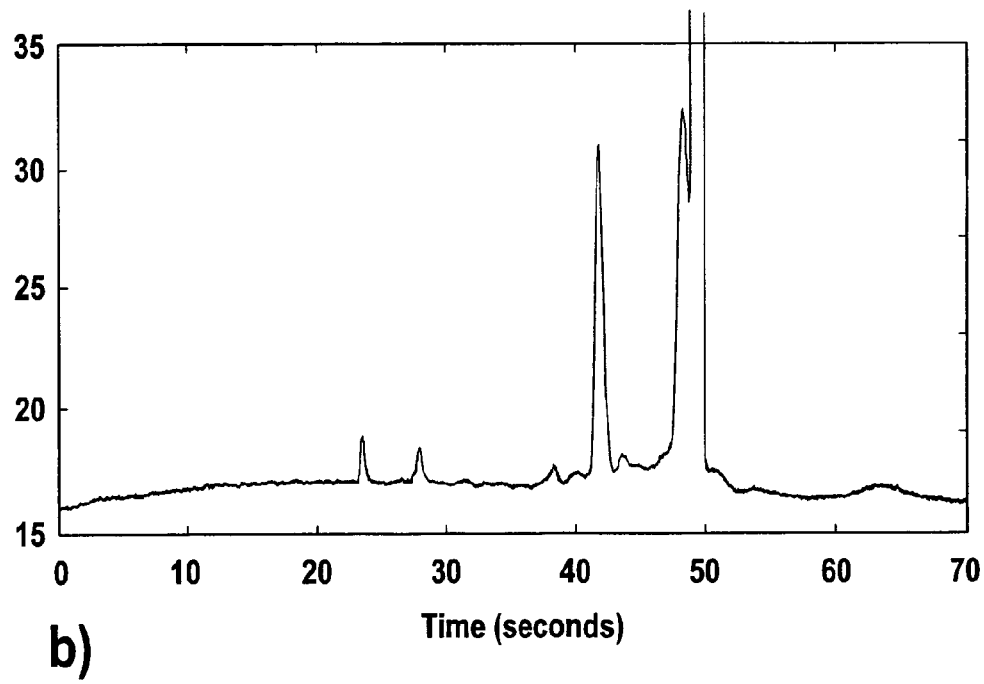

FIG. 9a depicts an electropherogram exhibiting a ghost peak superimposed on the true signal. The marker and the 18S-fragment and 28S-fragment are hardly recognizable. FIG. 9b depicts the same electropherogram, suitably rescaled. The marker and both of the ribosomal peaks are now readily recognizable.

Figure 10:
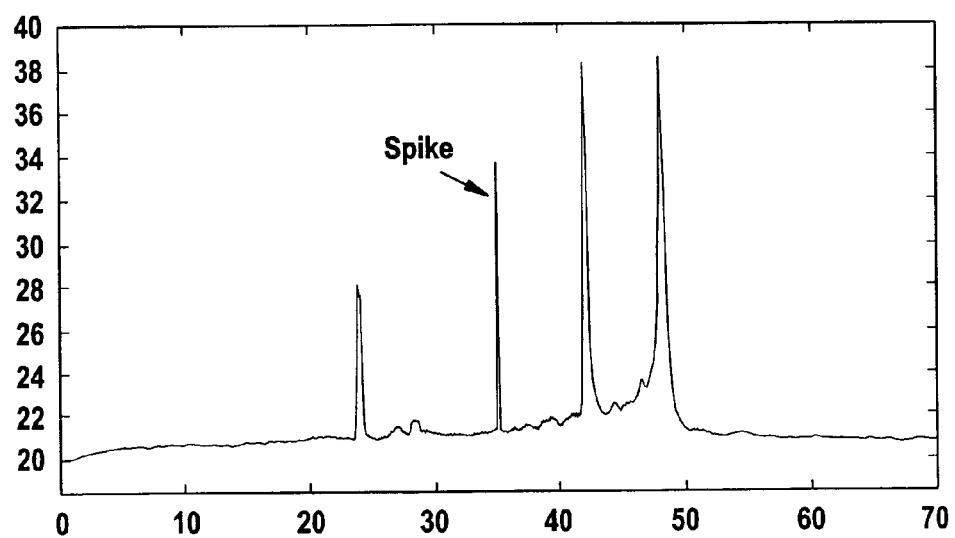

FIG. 10 depicts an electropherogram exhibiting a spike. Spikes are rarely occurring, tall peaks just a few data points wide.

Figure 11:
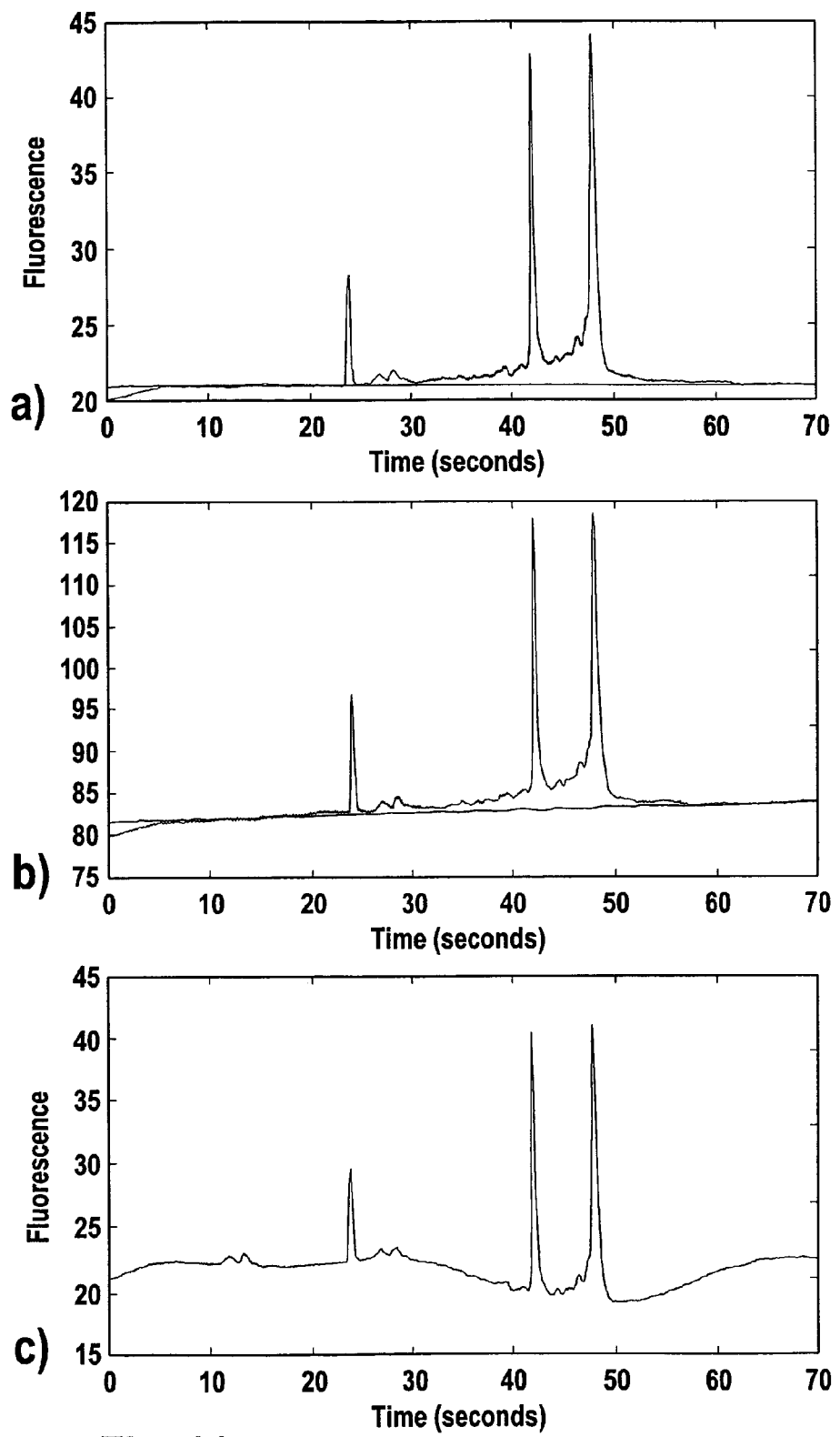

FIG. 11a depicts an electropherogram having an ideal, horizontal baseline. The baseline of the electropherogram shown in FIG. 11b has a pronounced slope, but will still be accepted. FIG. 11c depicts an electropherogram having a wavy baseline, which is an indication of problems occurring during data acquisition. These figures also illustrate the prominent variations in absolute fluorescence levels from chip to chip, as may be seen by comparing the baseline levels and marker heights appearing in the FIGS. 11a and 11b. The data analyses employed thus compute exclusively relative or normalized fluorescence levels.

Figure 12:
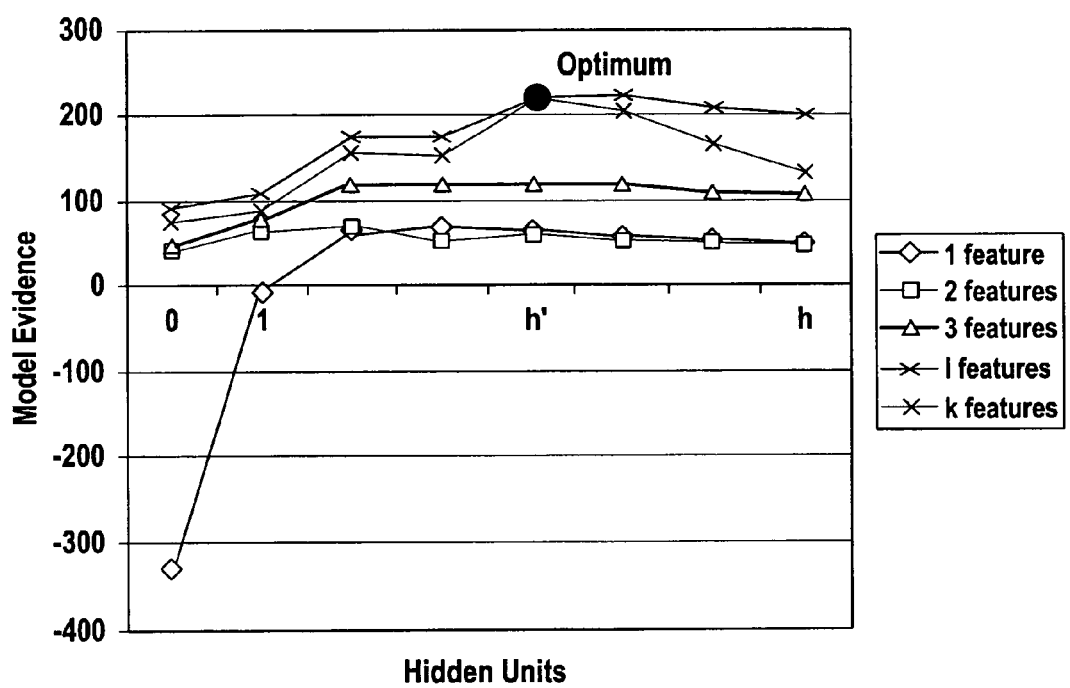

FIG. 12 illustrates the procedures involved in choosing models. Several models are trained to the feature vectors, $f_1$, $(f_1, f_2), \ldots, (f_1, \ldots, f_i), \ldots, (f_1, \ldots, f_n)$, using differing numbers, $1, \ldots, h$, of hidden neurons. A value of $h=7$ is more than sufficient for identifying anomalous cases and determining quality values. As models become more complex, i.e., as the numbers of features and hidden neurons employed are increased, the evidence will initially increase until the model is sufficiently complex for the task involved. The evidence will then decline, since the model will have become overly complex. The model having the greatest a posteriori probability, or evidence, is then chosen.

Figure 13:
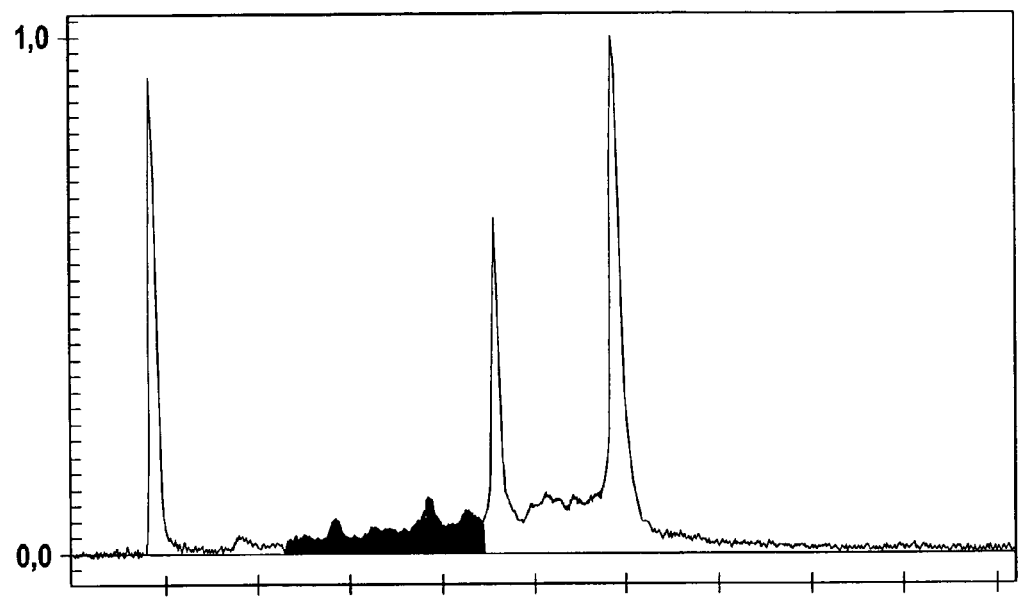
Figure 13:
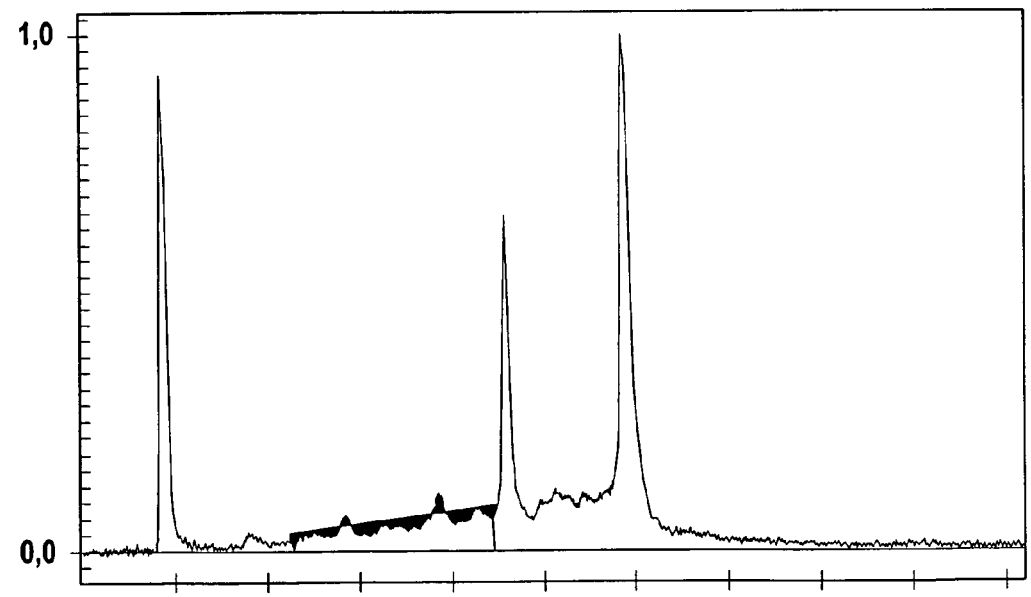

FIGS. 13a and 13b depict examples of features appearing in the fast region that have been extracted from the original data curve. Note that the maximum of the electropherogram has been normalized to 1.0. The maximum value and the minimum value of the data curve in the fast region are represented by points in FIG. 13a. The area under the data curve is shaded black. In FIG. 13b, the interpolating straight line is represented by a solid line and the ordinates of the interpolating solid lines at the end points of the fast region are represented by points. The deviations of the interpolating straight lines from the data curve are shaded black.

Figure 14:
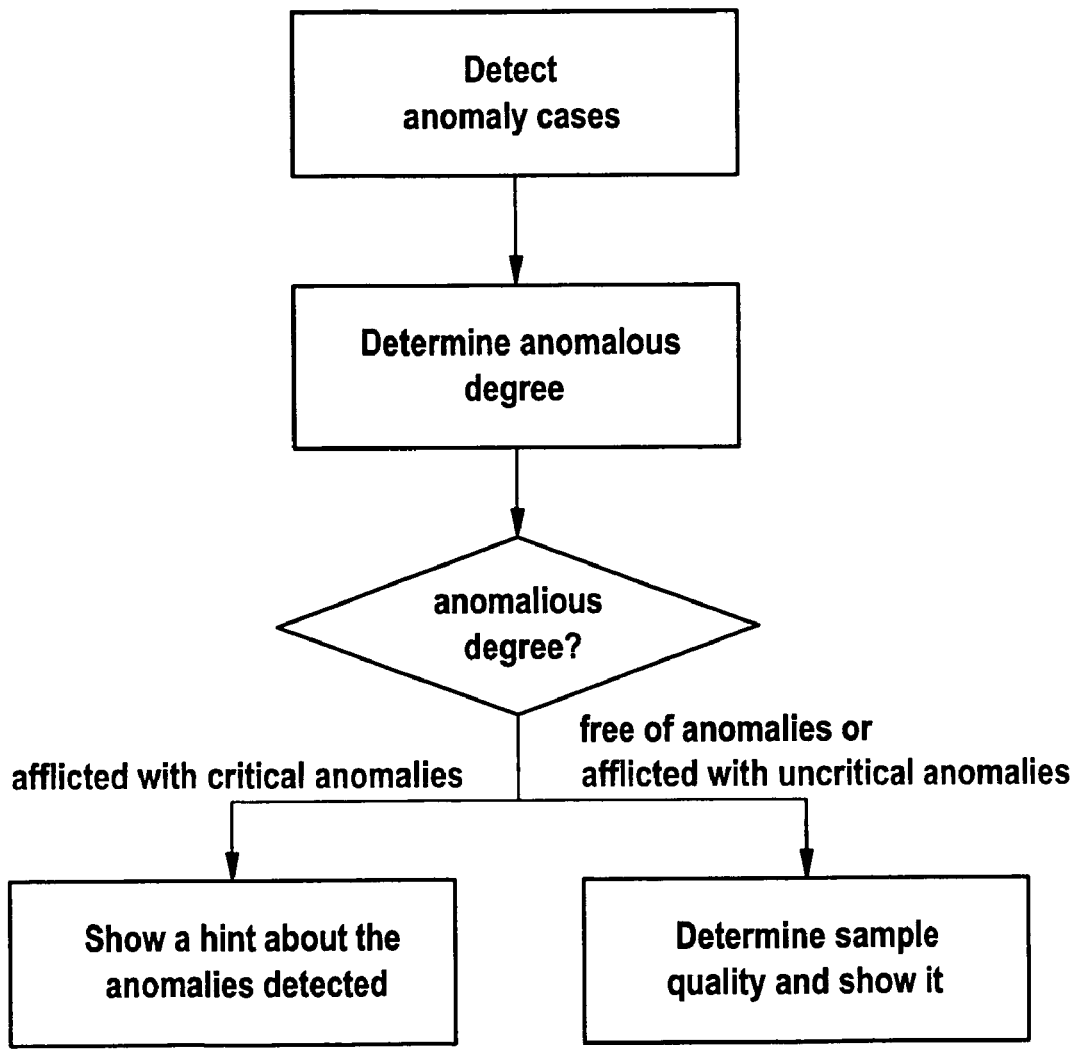

The flowchart shown in FIG. 14 illustrates the procedures involved in determining quality values and employing computed quality values that depend upon the computed degrees to which electropherograms suffer from anomalies. Outputting the quality values of electropherograms that are afflicted with anomalies makes little sense.

Figure 15:
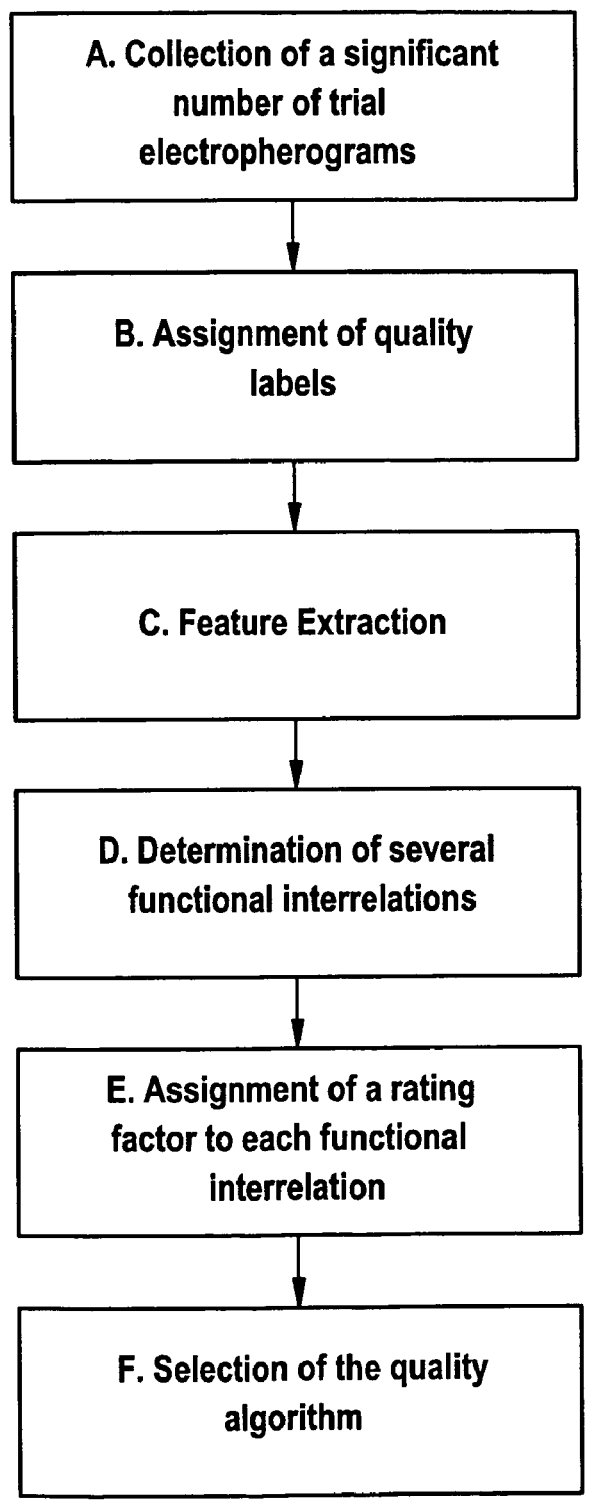

The flowchart shown in FIG. 15 illustrates the procedures involved in determining quality algorithms. These same procedures are employed for determining individual anomalous-case algorithms.

The invention claimed is:

1. A method for determining the extent of degradation, expressed in terms of a quality value, of an RNA sample, the method comprising:
    separating the RNA sample by mobility, using an electrophoresis device, to generate an electropherogram,
    extracting a number of prescribed features from the electropherogram using data analysis, and
    determining the quality value, which indicates the extent of degradation of the RNA sample, from the extracted features using a quality algorithm,
        wherein the quality algorithm has been derived from:
            collecting a statistically significant number of trial electropherograms covering a prescribed set of RNA samples,
            assigning a quality label, which indicates the extent that the trial electropherogram exhibits signs of degradation, to every trial electropherogram,
            extracting features from the trial electropherograms using data analysis,
            determining functional interrelations among the quality labels and one or more combinations of the extracted features,
            assigning a rating factor to every functional interrelation, and
            specifying the functional interrelation that has the highest rating factor as the quality algorithm.

2. The method of claim 1, further comprising:
    specifying one or more anomalous cases from among a prescribed number of potentially anomalous cases,
    extracting a number of prescribed features from the electropherogram of the RNA sample using data analysis for every anomalous case,
    analyzing the electropherogram using an associated anomalous-case algorithm in order to validate every anomalous case identified, and
    determining the magnitude of the anomaly involved from a combination of the anomalous cases present in order to determine the degree to which the RNA sample is anomalous.

3. The method of claim 2, wherein the following is carried out in order to determine the anomalous-case algorithm for a prescribed anomalous case:
    collecting a statistically significant number of trial electropherograms covering a prescribed set of RNA samples,
    assigning an anomalous-case label, which indicates the magnitude of anomaly, to the prescribed anomalous case of every trial electropherogram,
    extracting features from the trial electropherogram using data analysis, determining functional interrelations among the anomalous-case labels and one or more combinations of the extracted features, assigning a rating factor to every functional interrelation, and specifying the function interrelation that has the highest rating factor as the anomalous-case algorithm.

4. The method of claim 3, wherein the functional interrelations among the anomalous-case labels and the various combinations of extracted features are determined using an adaptive approach.

5. The method of claim 3, wherein 0 and 1 are prescribed as allowed values of the anomalous-case label.

6. The method of claim 3, wherein the extracted features are consecutively arranged in a list such that the information on the quality label and/or the anomalous-case label will be progressively maximized as each additional feature is added, where each addition of a feature to the list defines a new combination of features.

7. The method of claim 6, wherein the arrangement of extracted features in the list is based on mutual information.

8. The method of claim 1, wherein the functional interrelations among the quality labels and the various combinations of extracted features are determined using an adaptive approach.

9. The method of claim 8, wherein a neural network is employed as the adaptive approach.

10. The method of claim 9, wherein a Bayesian method is applied for adjusting parameters for the neural network.

11. The method of claim 10, wherein the a-posteriori probability of the neuronal network computed using a Bayesian method is employed as the rating factor.

12. The method of claim 9, wherein functional interrelations of varying complexity are determined, where the necessary complexity of the functional interrelations sought is obtained by iterative additions of hidden neurons to the neuronal network.

13. The method of claim 1, wherein discrete classes are established for the accessible range of electropherogram quality and every class is assigned a quality label.

14. The method of claim 13, wherein seven classes are established for the quality label.

15. The method of claim 1, wherein the electropherogram is first subdivided into segments before extracting features therefrom.

16. The method of claim 15, wherein the following eight regions of the electropherogram of the RNA sample are established as the segments: a preregion, a marker region, a 5S-region, a fast region, an 18S-region, an interregion, a 28S-region, and a postregion.

17. The method of claim 16, wherein one or more of the following prescribed features are determined in the data analysis of the electropherogram:

the ratio of the areas of the 18S-region segment and 28S-region segment to the total area enclosed within the eight segments, the ratio of the area of the 18S-region segment to the area of the 28S-region segment, or the signal/noise ratio.

18. The method of claim 15, wherein the electropherogram can be represented as a data curve or a smoothed data curve and wherein one or more of the following prescribed features of the segments of the data curve, or the smoothed data curve, of the electropherogram are determined in the data analysis of the electropherogram:

the maximum and minimum value occurring within the segment, the slope and y-intercept of the interpolating straight line fitted to the points on the curve falling within the bounds of the segment, the y-values of this interpolating straight line at the start and end points of the segment, the area under the curve, the area under the interpolating straight line, the ratios of the latter areas to the area under the entire data curve, the deviation of the interpolating straight line from the data curve, or the deviations of the original and smoothed data curve from one another.

19. The method of claim 18, wherein Savitzky-Golay filters and/or the rolling-ball algorithm are employed for smoothing the data curve.

20. The method of claim 1, wherein positions, heights, and widths of peaks occurring in the electropherogram are determined and their areas computed by integration under the data analysis performed on the electropherogram.

21. A non-transitory computer-readable data carrier, for executing or controlling a method for determining the extent of degradation, expressed in terms of a quality value, of an RNA sample based on an electropherogram of the RNA sample, the method comprising:

extracting a number of prescribed features from the electropherogram using data analysis, and determining the quality value, which indicates the extent of degradation of the RNA sample, from the extracted features using a quality algorithm, wherein the quality algorithm has been derived from:

collecting a statistically significant number of trial electropherograms covering a prescribed set of RNA samples, assigning a quality label, which indicates the extent that the trial electropherogram exhibits signs of degradation, to every trial electropherogram, extracting features from the trial electropherograms using data analysis, determining functional interrelations among the quality labels and one or more combinations of the extracted features, assigning a rating factor to every functional interrelation and specifying the functional interrelation that has the highest rating factor as the quality algorithm, when run on a data processing system such as a computer.

22. An apparatus for determining the extent of degradation, expressed in terms of a quality value, of an RNA sample, based on an electropherogram of the RNA sample, the apparatus comprising:

a processing unit adapted for extracting a number of prescribed features from the electropherogram using data analysis, and for determining the quality value, which indicates the extent of degradation of the RNA sample, from the extracted features using a quality algorithm, wherein the quality algorithm has been derived from:

collecting a statistically significant number of trial electropherograms covering a prescribed set of RNA samples, assigning a quality label, which indicates the extent that the trial electropherogram exhibits signs of degradation, to every trial electropherogram, extracting features from the trial electropherograms using data analysis, determining functional interrelations among the quality labels and one or more combinations of the extracted features, assigning a rating factor to every functional interrelation and specifying the functional interrelation that has the highest rating factor as the quality algorithm, when run on a data processing system such as a computer.

* * * * *